United States Patent
Kim et al.

(10) Patent No.: US 9,273,323 B2
(45) Date of Patent: Mar. 1, 2016

(54) COMPOSITION CONTAINING GENE ENCODING ABC TRANSPORTER PROTEINS FOR INCREASING SIZE OF PLANT SEED AND CONTENT OF FAT STORED WITHIN SEED

(75) Inventors: Sangwoo Kim, Phohang-si (KR); Youngsook Lee, Phohang-si (KR); Ikuo Nishida, Saitama (JP); Yasuyo Yamaoka, Saitama (JP); Hirofumi Ono, Saitama (JP)

(73) Assignee: POSTECH ACADEMY-INDUSTRY FOUNDATION, Pohang-si, Gyeonsangbuk-do (KR)

( * ) Notice: Subject to any disclaimer, the term of this patent is extended or adjusted under 35 U.S.C. 154(b) by 194 days.

(21) Appl. No.: 13/996,343

(22) PCT Filed: Sep. 16, 2011

(86) PCT No.: PCT/KR2011/006826
§ 371 (c)(1),
(2), (4) Date: Jun. 20, 2013

(87) PCT Pub. No.: WO2012/093764
PCT Pub. Date: Jul. 12, 2012

(65) Prior Publication Data
US 2013/0283481 A1    Oct. 24, 2013

(30) Foreign Application Priority Data
Jan. 6, 2011  (KR) .................. 10-2011-0001531

(51) Int. Cl.
*C12N 15/82*    (2006.01)
*C07K 14/415*   (2006.01)

(52) U.S. Cl.
CPC .......... *C12N 15/8261* (2013.01); *C07K 14/415* (2013.01); *C12N 15/8247* (2013.01)

(58) Field of Classification Search
None
See application file for complete search history.

(56) References Cited

U.S. PATENT DOCUMENTS

| 4,940,838 A | 7/1990 | Schilperoort et al. |
| 6,821,774 B1 | 11/2004 | Lawn et al. |
| 2009/0158452 A1* | 6/2009 | Johnson et al. ............... 800/260 |

FOREIGN PATENT DOCUMENTS

EP    0 120 516 B1    10/1991

OTHER PUBLICATIONS

Verrier et al, Plant ABC proteins—a unified nomenclature and updated inventory. Trends Plant Sci. 13:151-159, Apr. 2008. p. 153, left column, 2nd paragraph; supplement tables S1 and S2.*
Friedberg (Automated protein function prediction—the genomic challenge. Brief. Bioinformatics. 7: 225-242, 2006).*
Hill et al (Functional analysis of conserved histidines in ADP-glucose pyrophosphorylase from *Escherichia coli*. Biochem. Biophys. Res. Comm. 244:573-577, 1998).*
Guo et al (Protein tolerance to random amino acid change, Proc. Natl. Acad. Sci. USA 101:9205-9210, 2004).*
Uniprot:Q9FLT5; ibis internal exp.org/exam.
Takashi Kuromori et al. "ABC Transporter AtABCG25 is Involved in Abscisic acid transport and responses"; PNAS, Feb. 2, 2010, vol. 107, No. 5; 2361-2366.
Xiu-Hong-Xu et al. Mutations of the multi-drug resistance-associated protein ABC transporter gene 5 result in redution of phytic acids . . . ; Theor Appl Genet 2009 119:75-83.
Steve P. Slocombe et al "Oil accumulations in leaves directed by modification of fatty acid breakdown and lipid synthesis pathways" Plant Biotechnology Jour. (2009) 7, 694-703.
Sangwoo Kim et al. "AtABCA9 transporter supplies fatty acids for lipid synthesis to the endoplasmic reticulum" PNAS Jan. 8, 2013 vol. 110 No. 2; 773-778.
Paul J. Verrier et al "Plant ABC protiens—a unified nomenclature and updated inventory" Trends in Plant Science vol. 13 No. 4; 1360-1385.
European Search Report dated Dec. 8, 2014 re Application No. 11854771.0.
Takashi Kuromori et al; ABA Transport Factors Found in Arabidopsis ABC Transporters; Plant Signaling and Behavior, Sep. 2010; vol. 5-9; pp. 1124-1136.
Michal Jasinski et al; Full-Size ABC Transporters Form the ABCG Subfamily in Medicago Truncatula; Molecular Plant-Microbe Interactions; 2009; vol. 22; No. 8, pp. 921-931.
David Swarbreck et al; Isolation & Characterisation of Two Multidrug Resistance Associated Protein Gens from Maize; Science Direct; Gene 315; 2003; pp. 153-164.
Steven Clough et al; Floral Dip: A Simplified Method for Agrobacterium-Mediated Transformation of Arabidopsis Thaliana; The Plant Journal; 1998; pp. 735-743.
Markus Geisler et al; The ABC of Auxin Transport: The Role of P-Glycoproteins in Plant Development; FEBS Letters 580; 2006; pp. 1094-1102.
Paul J. Verrier et al; Plant ABC Proteins—A Unified Nomenclature and Updated Inventory; Trends in Plant Science; vol. 13, No. 4, 2008; pp. 151-159.

(Continued)

Primary Examiner — Medina A Ibrahim
Assistant Examiner — Wayne Zhong
(74) Attorney, Agent, or Firm — Lucas & Mercanti, LLP

(57) ABSTRACT

The present invention relates to a composition for increasing the size of a plant seed and the content of fat store within the seed, and more specifically to a composition containing a gene encoding ABC transporter proteins for increasing the size of a plant seed and the content of fat store within the seed, and a method for increasing the size of a plant seed and the content of fat store within the seed comprising a step of introducing said gene and a promoter for overexpressing said gene to a plant.

4 Claims, 11 Drawing Sheets

(56) References Cited

OTHER PUBLICATIONS

Cintia Hotta Orsi et al; Natural Variation in an ABC Transporter Gene Associated With Seed Size Evolution in Tomato Species; PLOS Genetics; vol. 5; Jan. 2009; pp. 1-12.

Toshio Murashige et al; A Revised Medium for Rapid Growth and Bio Assays With Tobacco Tissue Cultures; Physiologia Plantarium, vol. 15;1962; pp. 473-498.

H.A.B. Hiza et al; Nutrient Content of the U.S. Food Supply 2005; U.S.D.A.; Mar. 2008; pp. 1-72.

7-NCBI Gen Bank Accession AB9A-ARATH.

* cited by examiner

FIG. 1
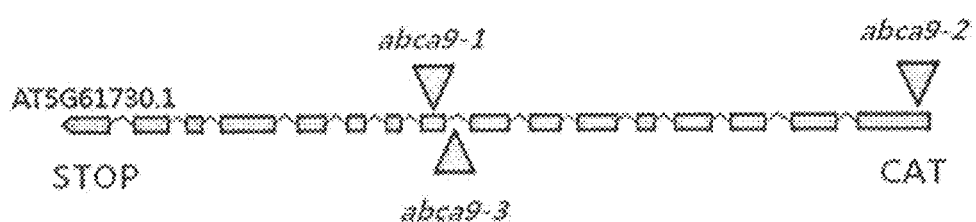
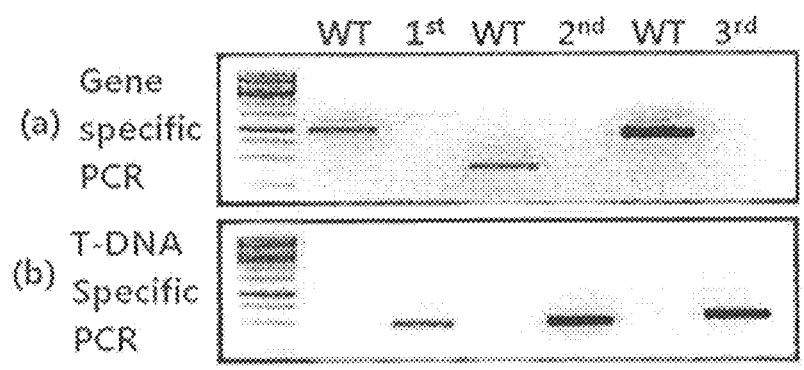

FIG. 3
1% sucrose
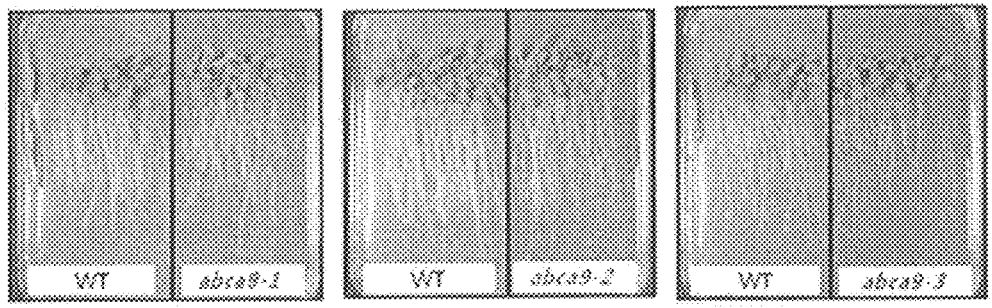
no sucrose
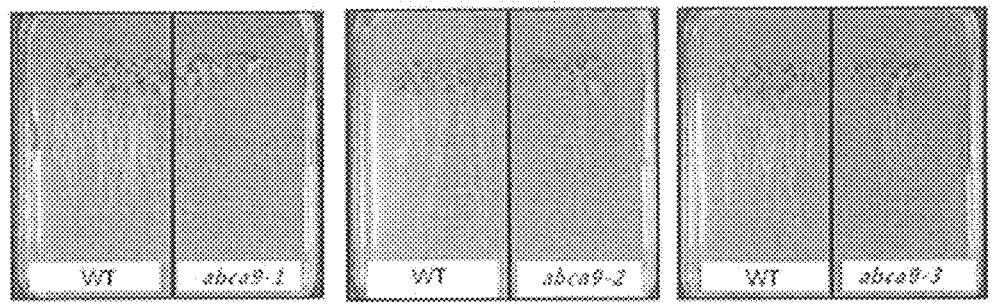

FIG. 4
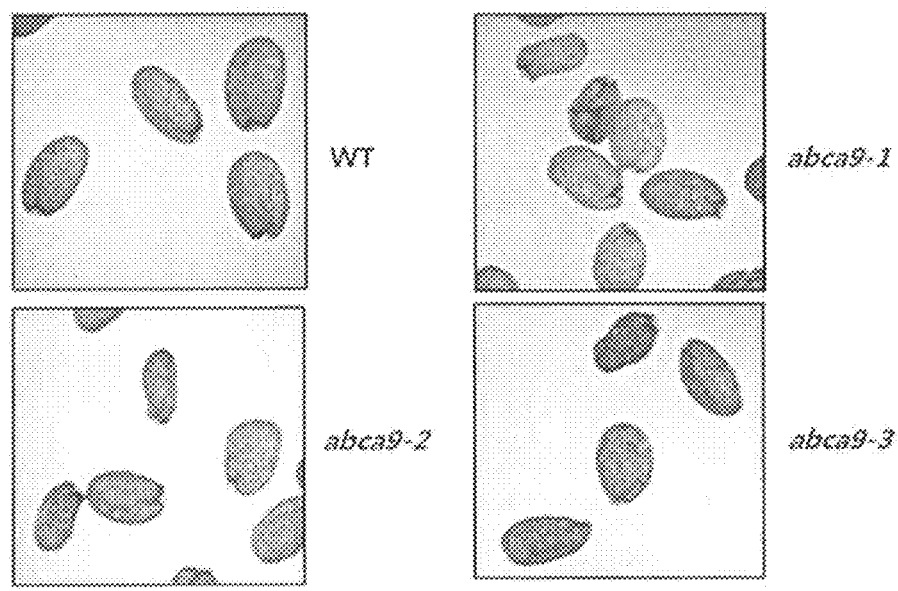
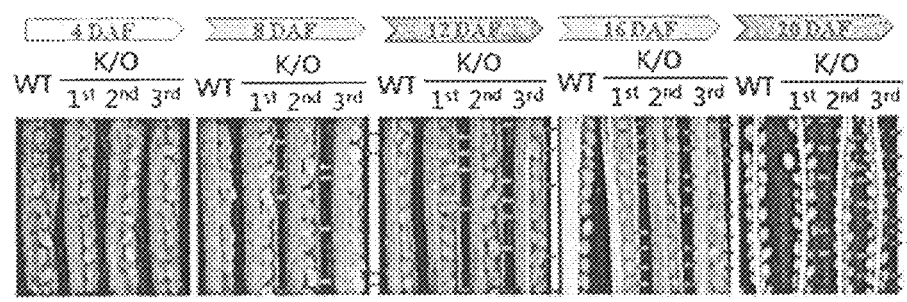

FIG. 5
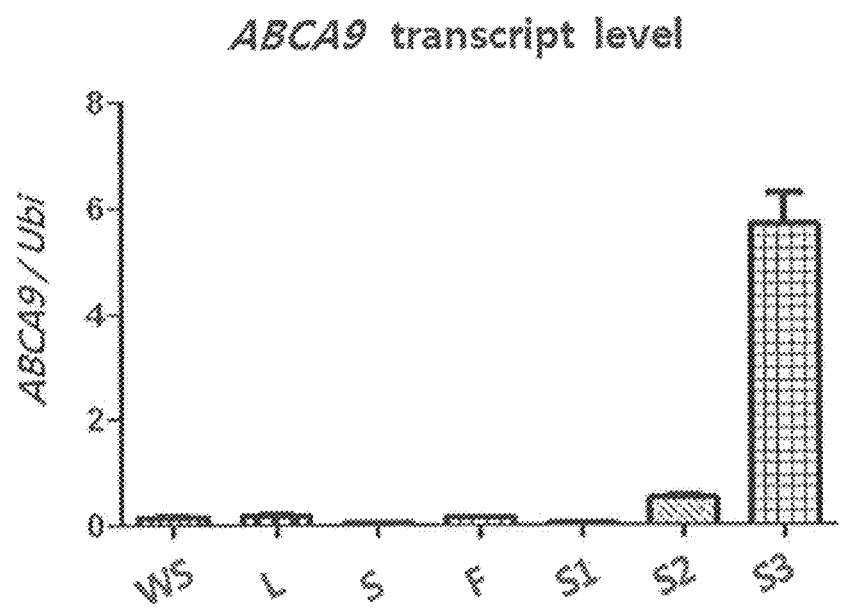
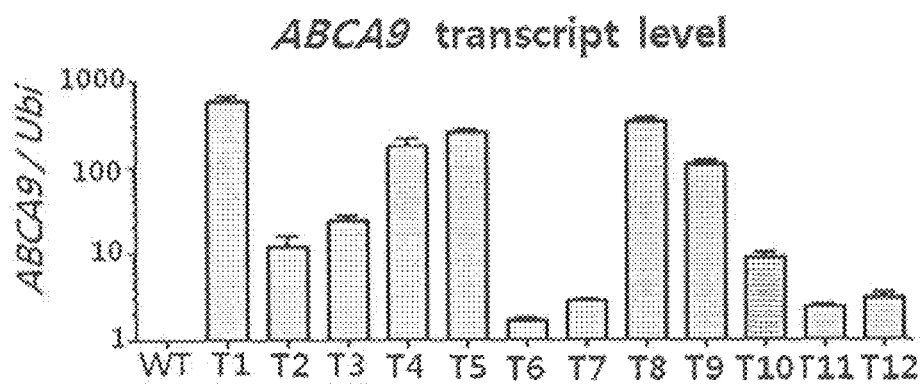

FIG. 6
a
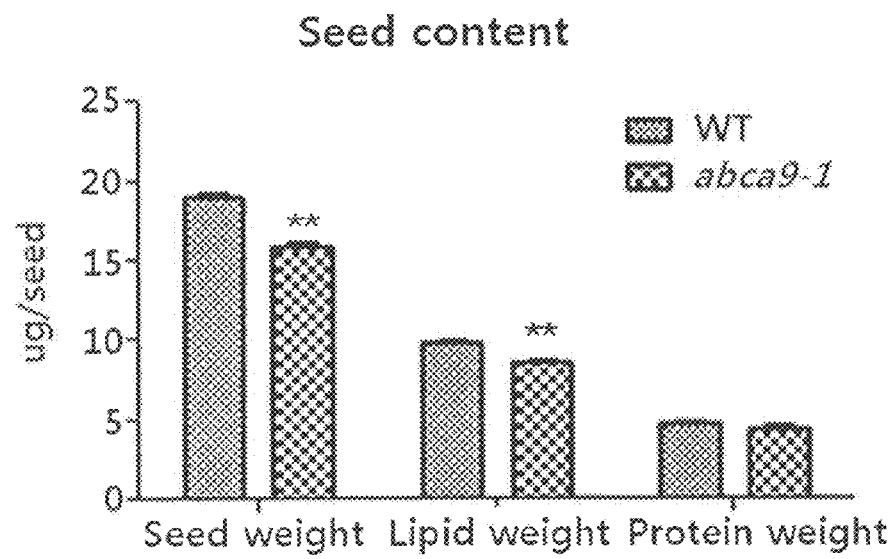
b
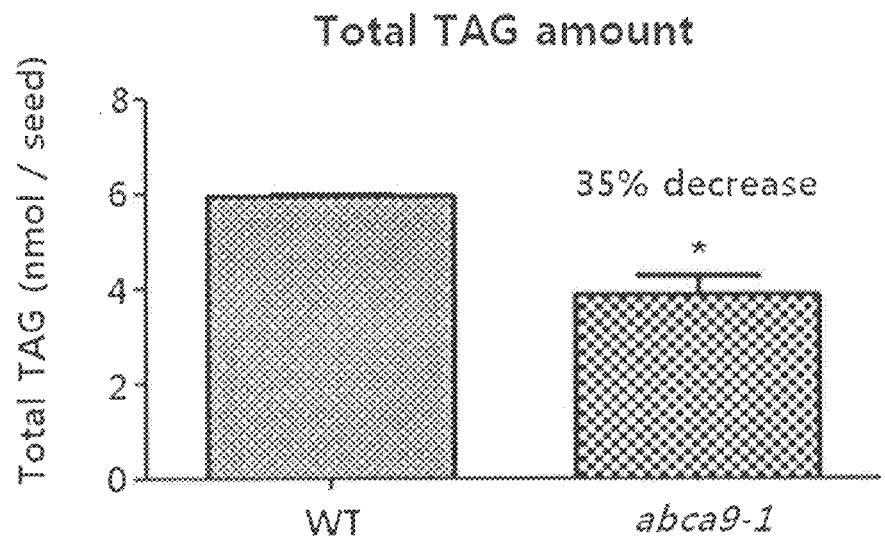

FIG. 9
a
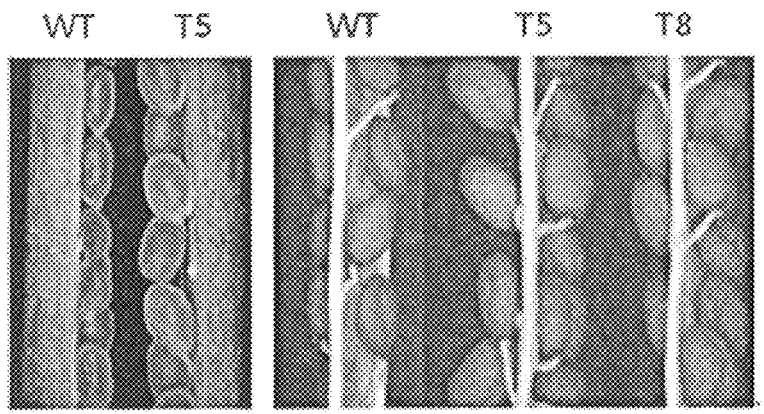
b
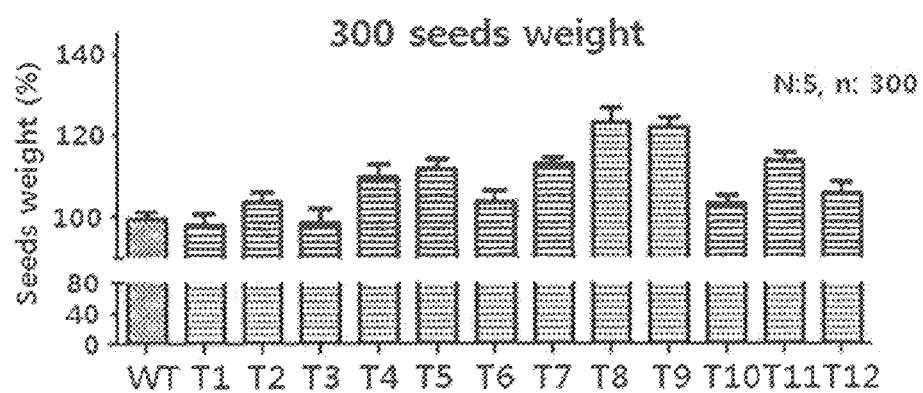
c
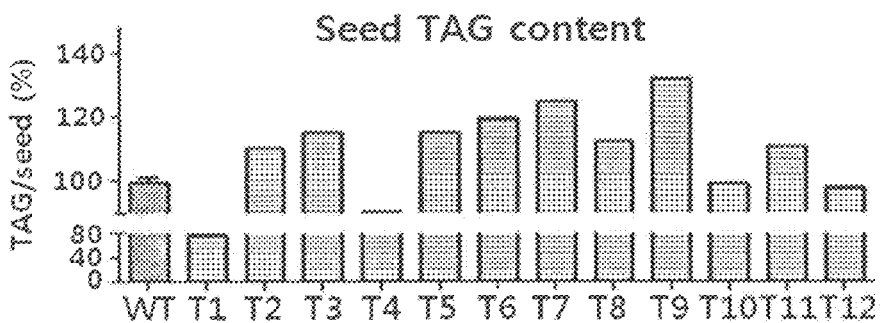

FIG. 10

MTLRBGLPLPHQQFTALFKKNLLLSWRNKRATCLHLPSSFFFILLIPSIRESSKASDL
TSTRHKNVTDPKALVSLPILPCEDKFFVRLPCFDFVWSGNQSRRVTDIVSAIMADNP
GRFPTNKYQSFTKPEEVDAWFMSHPSQYTGALHFVRKNATVISYGQTNSSSEKK
RGRREDPTFKFLVPLQIAABRBIARSLIGDPKFSWDFGPKEFARPAIGGEVIISAFVLM
GPVFFLAFSMFGFVLQLGSYVTEKELKLREAMTTMGYYESAYWLSWLIWBGILTFV
SSLFLVLFGMMFQFFFFLKNSFVLVFLLFFLFQFNMGLAFALSSIISKSSSATTVGFIL
VFLVGFITQIVTTAGFPYSSAYSIGSRVIWSLFPPNTFSAGLQLLLEATSSPQDSGISW
SBRAICAGGESTCVITTNKIYIWLVGTPFFWFVLALYFDNIIPNASGVRKSIFYFLKPS
YWTGKBGNKVEBGSICSCIGSVPPVBHITFEDEDVLBBBILVKQQAMDGRVDPNIAVQ
IHGLAKTYPGTTKLGCCKCTKTSPFHAVKGLWMNIAKDQLFCLLGPNGAGKTTTIS
CLTGINPVTGGDAKIYGNSIRSSVGMSNIRKMIGVCPQFDILVDALSSEBHLHLFASIK
GLPP2SIKSIABKLLVDVKLTGSAKIRAGSYSGGMKRRLSYAIALIGDPKLVFLDRPTT
GMDPITRRHVWDIIQBSKKGRAIILTTHSMEBADILSDRIGHAKGRLRCIGTSIRLKSR
FGTGFVATVSFIENKKDGAPEPLKRFFKERLKVBPTBBNKAFMTFVIPHDKBGLLKG
FFABLQDRBSEFGIADIQLGLATLRBVFLNIARRABLESATYBGTMYTLBLBSGIAVEI
PVGARFVGIPGTBNAENPRGLMVEVYWCQDGSGSMCISGHSAEMRIPENVSVIYBPS
SQVLGHGQRRVRGIVIDYESNN

FIG. 11

SEQUENCE LISTING

<160> NUMBER OF SEQ ID NOS: 11

<210> SEQ ID NO 1
<211> LENGTH: 950
<212> TYPE: PRT
<213> ORGANISM: Artificial Sequence
<220> FEATURE:
<223> OTHER INFORMATION: amino acid sequence of AtABCA9/AtATH11

<400> SEQUENCE: 1

```
Met Thr Leu Arg Glu Gly Leu Pro Leu Phe His Gln Gln Phe Thr Ala
 1               5                  10                  15

Leu Phe Lys Lys Asn Leu Leu Leu Ser Trp Arg Asn Lys Arg Ala Thr
            20                  25                  30

Cys Leu His Leu Phe Ser Ser Phe Phe Ile Leu Leu Ile Phe Ser
        35                  40                  45

Ile Glu Glu Ser Ser Lys Ala Ser Asp Leu Thr Ser Thr Arg His Lys
     50                  55                  60

Asn Val Thr Asp Pro Lys Ala Leu Val Ser Leu Pro Ile Leu Pro Cys
 65                  70                  75                  80

Glu Asp Lys Phe Phe Val Arg Leu Pro Cys Phe Asp Phe Val Trp Ser
                85                  90                  95

Gly Asn Gln Ser Arg Arg Val Thr Asp Ile Val Ser Ala Ile Met Ala
            100                 105                 110

Asn Asn Pro Gly Arg Pro Ile Pro Thr Asn Lys Val Gln Ser Phe Thr
        115                 120                 125

Lys Pro Glu Glu Val Asp Ala Trp Phe Met Ser His Pro Ser Gln Val
130                 135                 140

Thr Gly Ala Leu His Phe Val Glu Lys Asn Ala Thr Val Ile Ser Tyr
145                 150                 155                 160

Gly Ile Gln Thr Asn Ser Ser Ser Glu Lys Lys Arg Gly Arg Arg Glu
                165                 170                 175

Asp Pro Thr Phe Lys Phe Leu Val Pro Leu Gln Ile Ala Ala Glu Arg
            180                 185                 190

Glu Ile Ala Arg Ser Leu Ile Gly Asp Pro Lys Phe Ser Trp Asp Phe
        195                 200                 205

Gly Phe Lys Glu Phe Ala Arg Pro Ala Ile Gly Gly Glu Val Ile Ile
    210                 215                 220

Ser Ala Phe Tyr Leu Met Gly Pro Val Phe Phe Leu Ala Phe Ser Met
225                 230                 235                 240

Phe Gly Phe Val Leu Gln Leu Gly Ser Val Val Thr Glu Lys Glu Leu
                245                 250                 255

Lys Leu Arg Glu Ala Met Thr Thr Met Gly Val Tyr Glu Ser Ala Tyr
            260                 265                 270

Trp Leu Ser Trp Leu Ile Trp Glu Gly Ile Leu Thr Phe Val Ser Ser
        275                 280                 285

Leu Phe Leu Val Leu Phe Gly Met Met Phe Gln Phe Glu Phe Phe Leu
    290                 295                 300

Lys Asn Ser Phe Val Leu Val Phe Leu Leu Phe Leu Phe Gln Phe
305                 310                 315                 320

Asn Met Ile Gly Leu Ala Phe Ala Leu Ser Ser Ile Ile Ser Lys Ser
                325                 330                 335

Ser Ser Ala Thr Thr Val Gly Phe Leu Val Phe Leu Val Gly Phe Ile
            340                 345                 350

Thr Gln Ile Val Thr Thr Ala Gly Phe Pro Tyr Ser Ser Ala Tyr Ser
```

```
              355                 360                 365
Ile Gly Ser Arg Val Ile Trp Ser Leu Phe Pro Pro Asn Thr Phe Ser
    370                 375                 380

Ala Gly Leu Gln Leu Leu Glu Ala Thr Ser Ser Pro Gly Asp Ser
385                 390                 395                 400

Gly Ile Ser Trp Ser Glu Arg Ala Ile Cys Ala Gly Gly Glu Ser Thr
                    405                 410                 415

Cys Val Ile Thr Thr Asn Lys Ile Tyr Ile Trp Leu Val Gly Thr Phe
                420                 425                 430

Phe Phe Trp Phe Val Leu Ala Leu Tyr Phe Asp Asn Ile Ile Pro Asn
            435                 440                 445

Ala Ser Gly Val Arg Lys Ser Ile Phe Tyr Phe Leu Lys Pro Ser Tyr
        450                 455                 460

Trp Thr Gly Lys Glu Gly Asn Lys Val Glu Gly Ser Ile Cys Ser
465                 470                 475                 480

Cys Ile Gly Ser Val Pro Val Glu His Ile Thr Pro Glu Asp Glu
                485                 490                 495

Asp Val Leu Glu Glu Glu Ile Leu Val Lys Gln Gln Ala Met Asp Gly
                500                 505                 510

Arg Val Asp Pro Asn Ile Ala Val Gln Ile His Gly Leu Ala Lys Thr
            515                 520                 525

Tyr Pro Gly Thr Thr Lys Leu Gly Cys Cys Lys Cys Thr Lys Thr Ser
        530                 535                 540

Pro Phe His Ala Val Lys Gly Leu Trp Met Asn Ile Ala Lys Asp Gln
545                 550                 555                 560

Leu Phe Cys Leu Leu Gly Pro Asn Gly Ala Gly Lys Thr Thr Thr Ile
                565                 570                 575

Ser Cys Leu Thr Gly Ile Asn Pro Val Thr Gly Asp Ala Lys Ile
                580                 585                 590

Tyr Gly Asn Ser Ile Arg Ser Ser Val Gly Met Ser Asn Ile Arg Lys
            595                 600                 605

Met Ile Gly Val Cys Pro Gln Phe Asp Ile Leu Trp Asp Ala Leu Ser
        610                 615                 620

Ser Glu Glu His Leu His Leu Phe Ala Ser Ile Lys Gly Leu Pro Pro
625                 630                 635                 640

Ser Ser Ile Lys Ser Ile Ala Glu Lys Leu Leu Val Asp Val Lys Leu
                645                 650                 655

Thr Gly Ser Ala Lys Ile Arg Ala Gly Ser Tyr Ser Gly Gly Met Lys
                660                 665                 670

Arg Arg Leu Ser Val Ala Ile Ala Leu Ile Gly Asp Pro Lys Leu Val
            675                 680                 685

Phe Leu Asp Glu Pro Thr Thr Gly Met Asp Pro Ile Thr Arg Arg His
        690                 695                 700

Val Trp Asp Ile Ile Gln Glu Ser Lys Lys Gly Arg Ala Ile Ile Leu
705                 710                 715                 720

Thr Thr His Ser Met Glu Glu Ala Asp Ile Leu Ser Asp Arg Ile Gly
                725                 730                 735

Ile Met Ala Lys Gly Arg Leu Arg Cys Ile Gly Thr Ser Ile Arg Leu
                740                 745                 750

Lys Ser Arg Phe Gly Thr Gly Phe Val Ala Thr Val Ser Phe Ile Glu
            755                 760                 765

Asn Lys Lys Asp Gly Ala Pro Glu Pro Leu Lys Arg Phe Phe Lys Glu
        770                 775                 780
```

```
Arg Leu Lys Val Glu Pro Thr Glu Glu Asn Lys Ala Phe Met Thr Phe
785                 790                 795                 800

Val Ile Pro His Asp Lys Glu Gln Leu Leu Lys Gly Phe Phe Ala Glu
            805                 810                 815

Leu Gln Asp Arg Glu Ser Glu Phe Gly Ile Ala Asp Ile Gln Leu Gly
        820                 825                 830

Leu Ala Thr Leu Glu Glu Val Phe Leu Asn Ile Ala Arg Arg Ala Glu
        835                 840                 845

Leu Glu Ser Ala Thr Val Glu Gly Thr Met Val Thr Leu Glu Leu Glu
    850                 855                 860

Ser Gly Ile Ala Val Glu Ile Pro Val Gly Ala Arg Phe Val Gly Ile
865                 870                 875                 880

Pro Gly Thr Glu Asn Ala Glu Asn Pro Arg Gly Leu Met Val Glu Val
                885                 890                 895

Tyr Trp Gln Gln Asp Gly Ser Gly Ser Met Cys Ile Ser Gly His Ser
                900                 905                 910

Ala Glu Met Arg Ile Pro Glu Asn Val Ser Val Ile Tyr Glu Pro Ser
            915                 920                 925

Ser Gln Val Leu Gly His Gly Gln Arg Val Arg Gly Ile Val Ile
    930                 935                 940

Asp Tyr Glu Ser Asn Asn
945                 950

<210> SEQ ID NO 2
<211> LENGTH: 2853
<212> TYPE: DNA
<213> ORGANISM: Artificial Sequence
<220> FEATURE:
<223> OTHER INFORMATION: AtABCA9/AtATH11 gene

<400> SEQUENCE: 2
atgactctgc gagaaggctt gccgcttttt catcagcaat tcacagcttt gttcaagaag      60
aatctactgc tttcatggag gaacaagaga gccacgtgtc ttcatctctt ctcttcgttc     120
ttcttcatcc ttctcatctt ctctatagag gaatcttcca agcgagcga cttaaccctcg    180 actaggcaca gaatgtcac agatcctaaa gcattagtct ctcttccgat tcttccatgt      240
gaggataagt tttcgtgag acttccatgt tttgacttcg tgtggagtgg caaccagagc      300
cgtcgtgtca ctgacattgt ctctgcaatt atggctaaca atcctggacg accaattcca     360
accaataagg ttcaatcatt tacaaagcct gaggaagtag atgcatggtt tatgtcacat     420
ccatcgcaag taacaggggc tttgcatttt gtggaaaaga atgctacagt gatcagctat     480
ggaattcaaa caaactcttc atcggagaaa aaacgtggtc ggcgtgaaga tcctacgttt     540
aagttccttg ttcctcttca aattgctgca gagcgtgaaa tcgcaaggtc tttaattgga     600
gatccaaagt ttagttggga ttttggattt aaggaatttg cgcgtccagc gattggtggt     660
gaagtgatca tttctgcatt ttatcttatg ggaccagtgt tctttcttgc tttctccatg     720
tttggttttg ttctccaact cgggtctgtg gttaccgaga aagagctaaa acttcgcgag     780
gcaatgacaa cgatgggtgt ttatgaatct gcatattggt tgtcatggct catatgggaa     840
ggaatcctta cctttgtctc ctcactcttc ttggtcctct ttggaatgat gttccagttt     900 gagttttct tgaagaacag tttttgttctt gtcttcctac ttttcttttct ttttcagtttt     960 aatatgattg cctagcatt cgcgctatca tctatcatta gcaaatcatc ttcggcaaca    1020
actgttggtt tccttgtgtt tctggttggt tttataacac agattgtaac aactgctgga    1080
```

```
ttcccttatt caagcgcata ttcgattggt agccgtgtca tttggtcact ctttccaccg    1140 aataccttt  ctgcgggtct gcagctgctt cttgaagcga catcatctcc cggagactct    1200
ggaatcagtt ggagtgaaag agcaatatgt gcaggggggcg agagcacttg cgttattaca    1260
actaataaaa tctacatatg gctcgtggga acgttctttt tctggtttgt attggctctc    1320
tactttgaca acatcatccc caatgcatcc ggtgtgagaa aatcgatctt ctactttcta    1380
aaacctagtt attggactgg caagaaggc  aacaaagtgg aagaagggag catctgtagc    1440
tgtattggtt cagttccacc agtagagcat attacaccag aggacgaaga tgtgcttgaa    1500
gaggagattt tagttaaaca acaagcaatg gatggaagag ttgatcctaa cattgcagtt    1560
cagatacatg gtcttgcaaa gacatatcct ggaacaacaa agcttggatg ctgcaaatgc    1620
accaaaactt cgccttttca tgctgtaaag ggtttgtgga tgaatattgc caaagatcag    1680
ttgttttgtc ttctcggacc taatggcgca gggaaaacaa ctactattag ttgtttgact    1740
ggcataaatc cagtcactgg tggggatgca aaaatctatg gaaattccat aagaagctct    1800
gttggtatgt ccaacattcg taaaatgata ggagtttgtc ctcagtttga tattctttgg    1860
gatgctttgt ctagtgaaga gcacctccac ctctttgcta gcatcaaagg gttgccacca    1920
tcatcgatca aatcgattgc agagaagtta ctggtagatg tgaagctaac aggatcggcg    1980
aaaattagag caggaagtta cagtggtgga atgaaacgtc ggctgagtgt tgcaatagca    2040
ctcattggtg atcccaagct ggttttcta  gatgaaccga ctactggcat ggaccctatc    2100
acgaggagac atgtgtggga cattatacaa gagtcaaaga aggtcgtgc  catcatacta    2160 acgacgcatt ctatggagga agctgatatt ttaagtgatc gaataggat  catggctaaa    2220 ggcaggctcc gctgcattgg aacctcaatc aggttaaaat ctcgctttgg cacgggattt    2280
gttgctaccg ttagcttcat cgaaaacaaa aaagacggtg cacccgagcc attgaaaaga    2340
ttctttaagg agcgtctaaa agttgagcca acagaagaaa acaaagcttt catgactttt    2400
gtaatcccac acgacaaaga gcaacttttg aagggttttt tcgcggagct acaagataga    2460
gaatctgaat ttggtatcgc agacattcag ctcggtcttg ccactcttga agaagtgttt    2520
ttgaacatcg ctagacgtgc tgaactagaa agcgcaactt tgaaggaac  tatggtaact    2580 ctcgagttag aatcaggcat cgcagtcgag atacctgtgg gagcaagatt tgtaggtatc    2640
cctggaacag aaaacgcaga gaatccaaga ggactaatgg tggaagtgta ctggcaacaa    2700
gacgggtcag gatcgatgtg catttctgga cactcggcgg agatgcggat cccagagaat    2760
gtatcggtga tatatgaacc atcatcacaa gtattaggac atggacagcg acgagttcgg    2820
ggtattgtga ttgattatga atctaacaat taa                                 2853
```

<210> SEQ ID NO 3
<211> LENGTH: 23
<212> TYPE: DNA
<213> ORGANISM: Artificial Sequence
<220> FEATURE:
<223> OTHER INFORMATION: pROKLBb1

<400> SEQUENCE: 3
gcgtggaacc gcttgctgca act                                              23

<210> SEQ ID NO 4
<211> LENGTH: 21
<212> TYPE: DNA
<213> ORGANISM: Artificial Sequence
<220> FEATURE:

```
<223> OTHER INFORMATION: SALK_058070LP

<400> SEQUENCE: 4
ctacatatgg ctcgtgggaa c                                              21

<210> SEQ ID NO 5
<211> LENGTH: 21
<212> TYPE: DNA
<213> ORGANISM: Artificial Sequence
<220> FEATURE:
<223> OTHER INFORMATION: SALK_058070RP

<400> SEQUENCE: 5
aaagaggtgg aggtgctctt c                                              21

<210> SEQ ID NO 6
<211> LENGTH: 20
<212> TYPE: DNA
<213> ORGANISM: Artificial Sequence
<220> FEATURE:
<223> OTHER INFORMATION: SALK_084342LP

<400> SEQUENCE: 6
atgactctgc gagaaggctt                                                20

<210> SEQ ID NO 7
<211> LENGTH: 20
<212> TYPE: DNA
<213> ORGANISM: Artificial Sequence
<220> FEATURE:
<223> OTHER INFORMATION: SALK_084342RP

<400> SEQUENCE: 7
gaaagagacc aaaccacacc                                                20

<210> SEQ ID NO 8
<211> LENGTH: 26
<212> TYPE: DNA
<213> ORGANISM: Artificial Sequence
<220> FEATURE:
<223> OTHER INFORMATION: AtATH11-ATG primer

<400> SEQUENCE: 8
actagtatga ctctgcgaga aggctt                                         26

<210> SEQ ID NO 9
<211> LENGTH: 28
<212> TYPE: DNA
<213> ORGANISM: Artificial Sequence
<220> FEATURE:
<223> OTHER INFORMATION: AtATH11-Stop primer

<400> SEQUENCE: 9
actagtttaa ttgttagatt cataatca                                       28

<210> SEQ ID NO 10
<211> LENGTH: 20
<212> TYPE: DNA
<213> ORGANISM: Artificial Sequence
<220> FEATURE:
<223> OTHER INFORMATION: AtABCA9/AtATH11 F1 primer

<400> SEQUENCE: 10
atgactctgc gagaaggctt                                                20
```

```
<210> SEQ ID NO 11
<211> LENGTH: 20
<212> TYPE: DNA
<213> ORGANISM: Artificial Sequence
<220> FEATURE:
<223> OTHER INFORMATION: AtABCA9/AtATH11 R1 primer

<400> SEQUENCE: 11
catggaagaa tcggaagaga                                                    20
```

COMPOSITION CONTAINING GENE ENCODING ABC TRANSPORTER PROTEINS FOR INCREASING SIZE OF PLANT SEED AND CONTENT OF FAT STORED WITHIN SEED

CROSS REFERENCE TO RELATED APPLICATION

This Application is a 371 of PCT/KR2011/006826 filed on Sep. 16, 2011, which claims benefit of the priority of Korean Patent Application No. 10-2011-0001531 filed on Jan. 6, 2011, both applications are incorporated herein by reference in their entirety.

TECHNICAL FIELD

The present invention relates to a composition for increasing plant seeds in size or in content of fat store. More particularly, the present invention relates to a composition for increasing plant seeds in size or in content of fat store, comprising a gene coding for an ABC (ATP-binding cassette) transporter protein, and the method for increasing plant seeds in size or in content of fat store, comprising the step of introducing the gene, and a promoter for overexpressing the gene into a plant body.

BACKGROUND ART

Most plants store oil and fat in their seeds, with triacylglycerol being more predominant than other oil and fat forms. In plants, the first energy product is in the form of carbohydrate which are later converted and stored into triacylglycerol, a more dense form. Upon germination, 1 g of the stored oil is converted into 2.7 g of carbohydrate, which is directly used as an energy source during germination.

Vegetable oils are more abundant in unsaturated fatty acids compared to animal oils, and plants contain 18:2 and 18:3 fatty acids, and polyunsaturated derivatives thereof, which cannot be synthesized in animals. These fatty acids are called essential fatty acids, since they cannot be synthesized in vivo, and thus could be only ingested through food. In addition to the importance as food, vegetable oils are emerging as an alternative energy source, with extensive attention being paid as biodiesel due to the recent exhaustion of fossil fuel.

The production of oilseeds in the world amounted to 3.19 billion metric tons in 2001. While some are used directly as food, most of them are used for oil extraction. On average, the content of oil in oilseed accounts for roughly 26% of its total weight. Globally, the consumption of animal oil has been decreased or maintained since in 1970, while the consumption of vegetable oil has more than coupled between 1980 and 2000 (ca. 670 million tons), with a rapid increase in consumption tendency (refer to USDA food disappearance records, U.S. PUFA Consumption, 1909-2005).

As can be seen, the demand for vegetable oils tends to increase as days go by, while supply can't catch up the demand. To date, the output of oils from oilseeds has been maximized thanks to the continuous improvement in breeding and crossbreeding, and it is anticipated that with the current breeding and crossbreeding, it is difficult to catch up the demand in a limited cultivation area. As a solution to this limitation, genetically modified organisms have come to the fore. For the production of vegetable oil which is expected for tremendous worldwide demand, it is anticipated that developing genetically modified organisms with high oil output is essential. In this regard, many researchers around the globe are conducting research on increasing the oil content per unit weight of seed and increasing the total amount of oil, but many genes are complicatedly involved in triacylglycerol synthesis in the seed and the control process which take up most of the stored vegetable oil, and thus, the goal isn't being accomplished easily.

In order to improve the stored oil of plant seed, big multinational corporations, such as Monsanto and DuPont are conducting a research. But yet, accomplishments haven't been reported since although a fat content of a seed increases, there are lots of cases when the overall productivity decreases due to the reduction of overall plant growth and the number of silique. There is therefore a need to develop a gene that functions to allow an increase in oil content in a seed that mostly stores the vegetable oil, without decreasing the size of seeds or the number of siliques, or more ideally, increases both the size of seeds and the number of siliques. If this technology is developed, it can create higher values when applied in conjunction with other technologies developed in regards of plant fats. For example, the technology can be used to produce a greater amount of useful fats when it is applied to a plant producing omega-3 fatty acids or tocopherol or a certain useful fat/fatty acids, together with a technique of increasing the size of seeds and the number of siliques.

DISCLOSURE

Technical Problem

Accordingly, the present invention has been invented to solve the above problems occurring in the prior art, and an object of the present invention is to provide a composition for increasing plant seeds in size and in content of fat store, comprising more than one selected from the group consisting of an ABC (ATP-binding cassette) transporter protein and a gene encoding the ABC transporter protein.

Another object of the present invention is to a method for increasing plant seeds in size or in content of fat store, comprising the step of introducing a gene coding for ABC (ATP-binding cassette) transporter protein) and a promoter for overexpressing the gene into a plant.

Technical Solution

To fulfill the above purpose, the present inventors confirmed through research that when a gene coding for ABC (ATP-binding cassette) transporter protein is inserted and the gene is overexpressed, not only the size of the seeds of the transgenic plant increases, but also the fat store content itself inside the seeds increases, which eventually improves the stored fat store, thereby greatly increasing the productivity of seeds and fat store within seeds, and completed the invention.

In accordance with one aspect thereof, the present invention provides a composition for increasing plant seeds in size and in fat store content, comprising more than one selected from the group consisting of a plant ABC (ATP-binding cassette) transporter protein and a gene coding for the ABC transporter protein.

In accordance with another aspect thereof, the present invention provides a method for increasing plant seeds in size or in fat store content, comprising the step of introducing a gene coding for a plant (ATP-binding cassette) transporter protein, and a promoter for overexpression the gene into a plant.

In accordance with a further aspect thereof, the present invention provides a transgenic plant which bears seeds improved in size and in fat store content according to the method.

In accordance with still another aspect thereof, the present invention provides a seed which is improved in size and fat store content according to the method.

A detailed description will be given of the present invention, below.

In accordance with an aspect thereof, the present invention provides a composition for increasing plant seeds in size and in fat store content, comprising more than one selected from the group consisting of a plant ABC (ATP-binding cassette) transporter protein and a gene coding for the ABC transporter protein.

As used herein, the term "ABC (ATP-binding cassette) transporter protein" refers to a protein, composed of six biomembrane-spanning domains and one ATP-binding domain and positioned after passing through a biomembrane consisted of lipidic bilayer, and is a transporter that carried substances using the energy from ATP disintegration, and also plays a role of absorbing nutrition into the cell or transporting poisonous substance outside of the cell, and especially refers to a protein that directly or indirectly involves in transporting precursor for the synthesis of a vegetable fat (or oil).

The term "overexpression," as used herein, refers to expressing a gene encoding the ABC (ATP-binding cassette) transporter protein of the present invention at a higher level of that in a wild-type plant, and the method of overexpression may be performed using various well-known techniques, without particular limitations loaded thereto. For example, overexpression may be achieved by mutation in a ribosomal binding site, a promoter, or a regulatory region upstream of a structural gene or introduced to increase the number of appropriate gene copies, or an upstream from a structural gene introduced expression cassette can be worked in the same manner. Also, expression may be increased by introducing a gene inducible promoter encoding the ABC (ATP-binding cassette) transporter protein of the present invention or by extending the life of mRNA. A medium composition and/or changing the culturing technique can also overexpress the above gene.

The term "transformation" in the present invention means a molecular biological technique that changes the genetic trait of a cell by a DNA chain fragment or plasmid that possess a different type of foreign gene from that of the original cell have, penetrate among the cells and combine with the DNA that existed in the original cell. In the context of the present invention, transformation means that the above genes along with the overexpression promoter are inserted into the plant body.

The term "plant body," as used herein, may be selected from the group consisting of a plant, plant tissue, cell, and seed.

As used herein, the term "transformants" refers to the above plant body whose genetic trait has been altered through the above transformation.

The "plant cell" can be any cell of a plant. The plant cell may be a cultured cell, a cultured tissue, a cultured organ or a whole plant, preferably a cultured cell, a cultured tissue or a cultured organ, and more preferably any form of cultured cell.

The "plant tissue" is intended to encompass differentiated or undifferentiated plant tissues including, but not limited to, roots, stems, leaves, pollens, seeds, cancer tissue and various type of cells used in culture, that is, single cell, protoplast, sprout, and calluses. The plant tissue may be in planta, or may be in the status of organ culture, tissue culture or cell culture.

The expression "increase of seed in size," as used herein, is intended to preferably include, but not limited to the increase of plant seed and seed's weight, volume, number and size of silique, and the increase of yield and productivity thereof. The expression "increase of fat store content in a seed" refers to increasing the content of fat (or oil) stored in plant seed, and the increase of fat store content in the seed may preferably expand in meaning to, but not limited to, the increase of fat store content itself, but also the increase of fat store content in the seed and the productivity increase of vegetable fat (or oil) as a result, through the increase of seed in size.

The typical example of fat store in the above seed is triacylglycerols. A triacylglycerol (triacylglyceride; triglyceride) has a structure of one glycerol skeletal structure bound with three fatty acids, and is a principle component for both vegetable oil and animal fat. This triacylglycerols is transformed as energy source and used in animal upon scarce carbohydrate, and in plants, triacylglycerols is a representative fat store which is mainly stored in seed and used as nutrient upon seed germination.

The composition for increasing plant seeds in size or fat store content in accordance with the present invention is characterized by comprising an ABC transport protein, and this ABC transport protein may be preferably a polypeptide having the amino acid sequence of SEQ ID NO: 1 (AtABCA9/AtATH11 protein), but is not limited thereto.

Preferably, it may be a polypeptide composed of a homologous sequence with amino acid sequence of SEQ ID NO: 1 (AtABCA9/AtATH11 protein), and the homologous sequence may preferably share a homology of from 65% to 99%, more preferably from 80% to 99%, far more preferably from 90% to 99%, and most preferably from 90% to 95% or from 95% to 99% with the amino acid sequence of SEQ ID NO: 1.

Moreover, the gene encoding the polypeptide having the amino acid sequence of SEQ ID NO: 1, could preferably be, but not limited to the gene of SEQ ID NO: 2 (AtABCA9/AtATH11 gene) consisted of base sequence.

In addition to the gene, the composition may comprise the gene, a transformation vector inserted with a promoter for overexpressing the gene, or a microorganism transformed by the above transformation vector.

The term "transformation vector," as used herein, refers to a recombinant DNA molecule comprising the proper nucleic acid sequence which is essential for expressing coding sequence of interest and a coding sequence that is connected only to operate in specific host organism. The proper nucleic acid sequence may be a promoter, and may further comprise an enhancer, a transcriptional terminator, and a polyadenylation signal. Promoters, enhancers, transcriptional terminators, and polyadenylation signals which are available in eukaryotic cells are well known.

Examples of the promoter is a promoter for plant expression which can use CaMV (Cauliflower Mosaic Virus) 35S promoter, NOS (nopaline synthase) promoter of *Agrobacterium tumefaciens* Ti plasmid, OCS (octopine synthase) promoter and MAS (mannopine synthase) promoter, but are not limited thereto.

The transcriptional terminator may use typical one examples of which include nopaline synthase (NOS), rice α-amylase RAmy1 A terminator, phaseoline terminator, and a terminator for optopine gene of *Agrobacterium tumefaciens*, but are not limited thereto.

Preferably, the transformation vector may further comprise a marker for identifying the gene expression or selecting a transformants. The marker is a nucleotide sequence typically having a property based on which it can be selected by a common chemical method, and any gene that is available to differentiate transformed cells from non-transformed cells can be a marker. Marker gene may include a gene resistant to an antibiotic such as kanamycin, spectinomycin, or a gene encoding GUS (β-glucuronidase), but are not limited thereto. The marker is delivered to a plant together with the vector, and is cultivated in a medium which contains a specific antibiotic and allows selecting transformants.

The transformation vector may be a plant expression vector in which a base sequence of the gene is inserted and be directly introduced into a plant cell or be introduced into a microorganism that trigger infection to a plant.

A preferred embodiment of the plant expression vector is a Ti-plasmid vector, which can transfer its segment, known as T-region, to plant cell when existing in a proper host such as *Agrobacterium tumefaciens*. There are many strains of *Agrobacterium* that can be used in this manipulation and are known in the art. Another type of T-plasmid vector is used as transferring hybrid DNA sequence, and is a protoplast which can produce a new plant that properly inserts the present plant cell or a hybrid DNA sequence into a plant's genome.

Another preferred type of the Ti-plasmid vector is a binary vector disclosed in EP 0120516 B1 and U.S. Pat. No. 4,940, 838. Another proper vector which can be used to introduce the gene according to the present invention into a plant host may be selected from among virus vectors that can be derived from double stranded plant viruses including CaMV, single stranded viruses, and geminiviruses, for example, a non-complete plant virus vector. Use of these vectors may be especially advantageous when it is difficult to properly transform a plant host. Most preferred may be a pCAMBIA1302 vector with a cauliflower mosaic virus (CaMV) 35S promoter.

More particularly, the vector may be pCAMBIA1302:: AtABCA9/AtATH11 gene which may comprise a 35S promoter, an AtABCA9/AtATH11 gene, and a nophaline synthase transcription terminator.

So long as it causes an infection in plants, any microorganism may be used without limitation in the present invention. For example, various viruses or bacteria may be employed, preferably, the soil bacterium, *Agrobacterium tumefaciens*, which causes crown gall disease in dicotyledonous plant.

The plants may be, for example, herbaceous plants and/or woody plants and may be flowering plants, garden plants, rice, wheat, barley, corn, soybean, red bean, oat, sorghum, onion, carrot, cucumber, olive, sweet potato, potato, Chinese cabbage, radish, lettuce, broccoli, tobacco, petunia, sunflower, leaf mustard, turf, *Arabidopsis, Brassica campestris, B. napus, Betula platyphylla*, poplar, hybrid poplar, and *Betula schmidtii*.

According to another exemplary embodiment of the present invention, the present invention provides a method for increasing plant seeds in size or fat store content, comprising the step of introducing a gene coding for a plant ABC (ATP-binding cassette) transporter protein, and a promoter for overexpressing the gene into a plant body.

The ABC transport protein may be preferably a polypeptide having the amino acid sequence of SEQ ID NO: 1 (AtABCA9/AtATH11 protein), but is not limited thereto.

As for the gene encoding the polypeptide having the amino acid sequence of SEQ ID NO: 1, could preferably be but limited to, SEQ ID NO: 2 (AtABCA9/AtATH11 gene) gene which is consisted of base sequence.

In order to introduce the gene into a plant body, an *Agrobacterium tumefaciens*-mediated gene transfer method may be preferably used, and more preferably, may use recombinant *Agrobacterium* dipping method which is produced through selecting the method among electroporation, microparticle injection and gene gun, but is not limited thereto.

According to further another exemplary embodiment of the present invention, the present invention provides a plant body which is increased in seed size and fat store content in the seed according to the method of increasing the seed size of the plant or the fat store content of the seed.

The plant body may be preferably selected from the group consisting of a whole plant, a plant tissue, a plant cell, and a plant seed.

According to still another exemplary embodiment of the present invention, the present invention provides a seed which is increased in size or fat store content according to the method of increasing the seed size of the plant or the fat store content of the seed.

Advantageous Effects

The composition for increasing the plant seed size and fat store content in the seed and the method for increasing plant seeds in size or fat store content according to the present invention can be used to increase the size of the plant seed of course, and the weight, and volume of the seed, the number and size of siliques, and thereby improving seed yield and productivity. Moreover, increases not only the content of stored fat (or oil) in seeds itself, but also more increases the fat store content in the seed through increasing the size of the seed which is a main storage organ of the plant oil as stated, and thus making a significant contribution to the supply of biodiesel and edible plant fats (or oils) in response to the rapidly increasing demand.

DESCRIPTION OF DRAWINGS

FIG. 1 shows three different mutants according to Example 1, and FIG. 1a shows three different alleles (abca9-1/ath11-1. abca9-2/ath11-2, abca9-3/ath11-3) with T-DNA to produce AtABCA9/AtATH11 gene mutant *Arabidopsis thaliana*, FIG. 1b shows the result of running gene-specific PCR (a) and T-DNA-specific PCR (b) according to Example 1 to examine the knockout due to the insertion of T-DNA. (WT: wild-type; $1^{st}$: abca9-1, $2^{nd}$: abca9-2, $3^{rd}$: abca9-3).

FIG. 3 shows the result of comparing the growth of the three different mutants that can't express AtABCA9/AtATH11 protein and the wild species in accordance with Example 2-2.

FIG. 4a shows the result of comparing wild species and the seeds of three different mutants that can't express AtABCA9/AtATH11 protein in accordance with Example 3, and FIG. 4b shows the result of observing the inside of the siliques of the wild species and the three different mutants that can't express AtABCA9/AtATH11 protein ($1^{st}$: abca9-1, $2^{nd}$: abca9-2, $3^{rd}$: abca9-3) as observed every 4 days after flowering (4, 8, 12, 16, and 20 DAF (Day After Flowering)) in accordance with Example 3.

FIG. 5a is a graph showing the result confirmed through quantitative RT-PCR by classifying the expression of AtABCA9/AtATH11 protein in organizations (WS: whole seedling), L: leaf, S: stem, F: flower, S1: silique 4~6 DAF, S2: silique 10~12 DAF, and S3: silique 16~18, DAF: (Day After Flowering)), in accordance with Example 5, and FIG. 5b is a graph showing the expression levels of the overexpression transformants through quantitative RT-PCR (WT: wild-type, T1~T12: overexpression transformants) in accordance with Example 5.

FIGS. 6a and 6b show the result of measuring fat store in a seed in accordance with Example 6.

FIGS. 9a to 9c each shows the result of measuring siliques (FIG. 9a), the weight of seeds (FIG. 9b), and the content of TAG of the seed (FIG. 9c) inside the silique of wild species and overexpressing transformants in accordance with Example 7 (WT: wild-type, T1-T12 overexpression transformants).

FIG. 10 shows the amino acid of sequence ID No:1 consisting the ABC transporter protein of the present invention.

Figure 11:
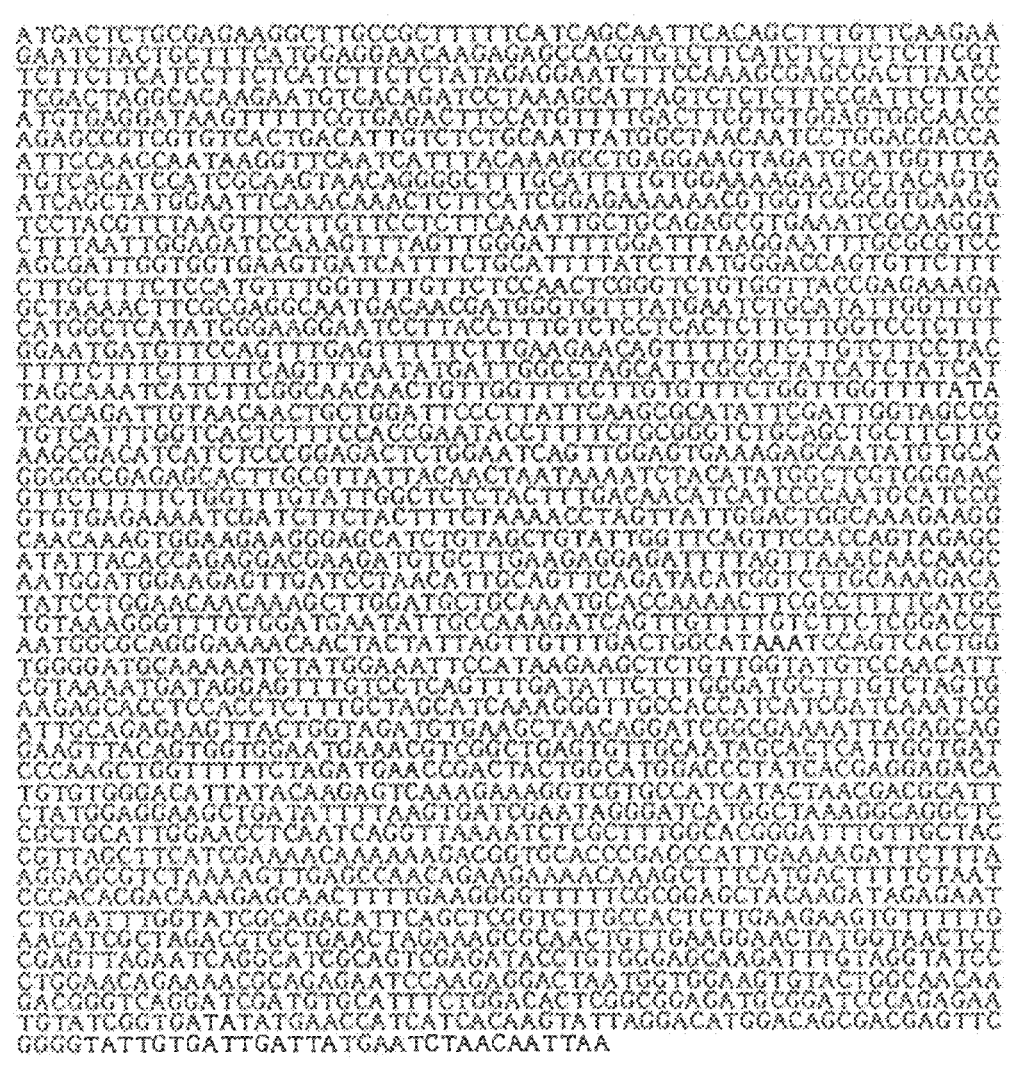

FIG. 11 shows the base sequence of sequence ID No:2 consisting the gene encoding ABC transporter protein of the present invention.

BEST MODE

Figure 2:
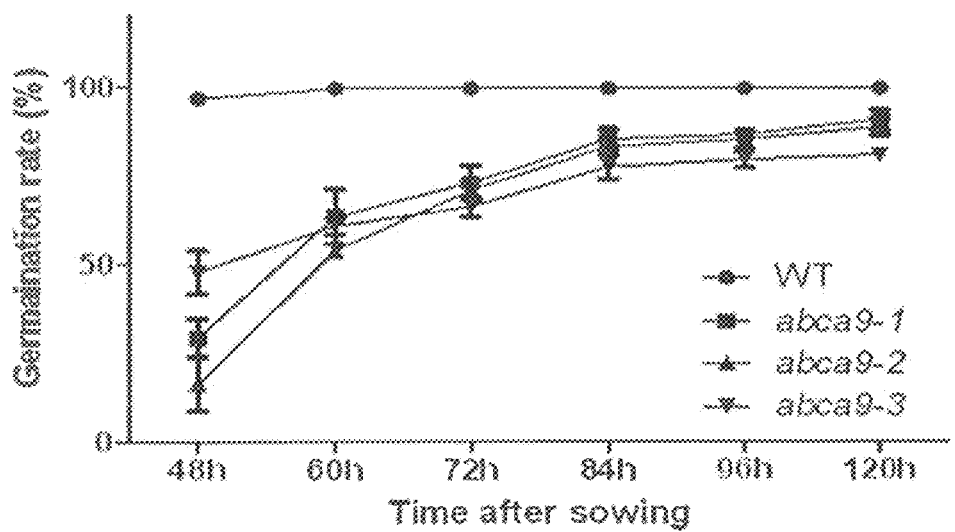
FIG. 2 shows the result of measuring the germination rates of the three different mutants that can't express AtABCA9/AtATH11 protein and the wild species in accordance with Example 2-1.

Hereinafter, preferred embodiments of the present invention will be presented for a better understanding of the present invention. However, the description proposed herein is just an example for a better understanding, not intended to limit the scope of the invention.

Reference Example 1

Isolation of Genomic DNA (gDNA)

Genomic DNA was extracted using a DNA extraction buffer (50 mM Tris-HCl, 10 mM EDTA, 100 mM NaCl, 1% (v/v) SDS, 10 mM β-mercaptoethanol) from leaves of *Arabidopsis thaliana* (wild-type (Columbia-0, SALK institute) and mutant) cultured for 2 weeks in a ½ MS medium (Murashige and Skoog, 1962).

In detail, leaves of *Arabidopsis thaliana* were homogenously pulverized using liquid nitrogen, and mixed with 750 µl of the DNA extraction buffer per 1 g of the pulverized sample by vortexing, followed by incubation at 65° C. for 30 min. Subsequently, 250 µl of 5 M potassium acetate was added to the sample and was shaken, cooled for 20 minutes in ies, and centrifugation was processed at 12000 rpm in 4° C. for 10 min. The supernatant was transferred to a fresh tube, and 700 µl of isopropanol was added and shaken slightly. The pellet formed after removing supernatant through centrifugation at 12000 rpm, in 4° C. for 10 min, was washed with 80% (v/v) ethanol and then dried. It was dissolved in 50 µl of a TE buffer and separated genomic DNA and was used in PCR, etc.

Example 1

Isolation of *Arabidopsis thaliana* that can't Express AtABCA9tAtATH11 Protein

To search for a mutant incapable of expressing AtABCA9/AtATH11 protein due to the insertion of T-DNA into the AtABCA9/AtATH11 gene, a mutant with T-DNA inserted in three different sites was ordered from SALK Institute (http://signal.salk.edu/) (FIG. 1a) The three mutants ordered were SALK_058070: abca9-1, SALK_084342:abca9-2, and SALK_023744:abca9-3, and the three mutants and wild-type (Columbia-0, SALK institute) *Arabidopsis thaliana* were cultured for 2 weeks in a ½ MS medium (Murashige and Skoog, 1962) containing kanamycin and extracted genomic DNA of each and identified the knockout status of genes.

In detail, the genomic DNA extracted from the Example 1 method was the template and performed the gene (AtABCA9/AtATH11)-specific PCR and T-DNA-specific PCR response, and for the PCR response, the following primers were used.

<List of Primers Used>

```
1. pROKLBb1 (SEQ ID NO: 3:
5'-GCGTGGAACCGCTTGCTGCAACT-3')

2. SALK_058070LP (SEQ ID NO: 4:
5'-CTACATATGGCTCGTGGGAAC-3')

3. SALK_058070RP (SEQ ID NO: 5:
5'-AAAGAGGTGGAGGTGCTCTTC-3')

4. SALK_084342LP (SEQ ID NO: 6:
5'-ATGACTCTGCGAGAAGGCTT-3')

5. SALK_084342RP (SEQ ID NO: 7:
5'-GAAAGAGACCAAACCACACC-3'F)
```

In this list, the pROKLBb1 primer of 1 was specific for T-DNA while all the primers of 2 to 5 were specific for the gene AtABCA9/AtATH11.

In SALK_058070: for the gene-specific PCR of abca9-1, no. 2 of the list was used as a forward primer and no. 3 as a reverse primer, and for T-DNA-specific PCR, no. 1 was used as a forward primer and no. 3 as a reverse primer.

In SALK_084342: for the gene-specific PCR of abca9-2, no. 4 of the list was used as a forward primer and no. 5 as a reverse primer, and for T-DNA-specific PCR, no. 1 was used as a forward primer and no. 5 as a reverse primer.

In SALK_023744: for the gene-specific PCR of abca9-3, no. 2 of the list was used as a forward primer and no. 3 as a reverse primer, and for T-DNA-specific PCR, no. 2 was used as a forward primer and no. 1 as a reverse primer.

By performing PCR (35 cycles of 95° C. 30 sec, 56° C. 30 sec, and 72° C. 30 sec) using each primers as described above, a mutant in which T-DNA was inserted as a homozygote into the AtABCA9/AtATH11 gene was excavated (FIGS. 1a and 1b).

In detail, as a result of performing gene specific PCR using primer pairs specific for the gene (AtABCA9/AtATH11), band that becomes PCR only in wild-type (WT) was identified ((a) of FIG. 1b), and as a result of performing T-DNA specific PCR using RP or LP primers specific for each gene (abca9-1, abca9-2: RP, abca9-3: LP) and primers specific for T-DNA, band that only becomes PCR in knockout lanes was identified and excavated mutants in which T-DNA was inserted as a homozygote.

Example 2

Effect of AtABCA9/AtATH11 Gene on Germination and Growth of Plant

Example 2-1

Effectiveness Measurement on Germination Rate

To measure germination rates of *Arabidopsis thaliana* mutants that can't express AtABCA9/AtATH11 protein (abca9-1, abca9-2, abca9-3) identified in Example 1 and the wild-type (Columbia-0, SALK institute), each seeds were planted in a ½ MS medium (Murashige and Skoog, 1962), and was monitored after 48 hrs at intervals of 12 hrs by optical microscopy.

Germination was determined on the basis of the emergence of radicles.

The observation result, as shown in FIG. 2, while the wild-type was 98% germinated after 48 hrs since the seed was planted in the medium, the mutant that can't express AtABCA9/AtATH11 protein showed late germination comparing to wild-type due to small and crumpled seed, and even if it was germinated, only 20~40% were germinated, and roughly 20% of the mutant did not germinate to the end.

Example 2-2 Effectiveness Measurement on Growth

To measure growth rates of *Arabidopsis thaliana* mutants that can't express AtABCA9/AtATH11 protein (abca9-1, abca9-2, abca9-3) identified in Example 1 and the wild-type (Columbia-0, SALK institute), each seeds were planted in rich media containing sucrose and a sucrose-free media of ½ MS media (Murashige et al., 1962, Duchefa), and after cultivated for 3 weeks, the growth was observed and measured the effect on the growth of *Arabidopsis thaliana*

As a result shown in FIG. 3, there were no differences between the wild-type and the three different mutants that can't express AtABCA9/AtATH11 protein in the rich media containing 1% of sucrose, while when there isn't a sucrose and should germinate and grow fully using the nutrients in the seed, the mutants that can't express AtABCA9/AtATH11 protein showed slow growth and couldn't grow well compared to wild-type.

Example 3

Effect Measurement on the Seed of AtABCA9/AtATH11 Gene

As a result of observing the seed of *Arabidopsis thaliana* mutants (abca9-1, abca9-2, abca9-3) that can't express the AtABCA9/AtATH11 protein identified in Example 1, it was identified that it produced a far greater number of small and rumpled seeds compared to the wild-type (Columbia-0, SALK institute) (FIG. 4a), and when observing the seed inside the siliques of the wild-type and three different mutants that can't express AtABCA9/AtATH11 protein at intervals of 4 days after flowering (4, 8, 12, 16, and 20 DAF (Day After Flowering)), three different mutants that can't express AtABCA9/AtATH11 protein produced small, pale colored seeds from earlier times compared to the wild-type and eventually produced more small and rumpled seeds which indicated that AtABCA9/AtATH11 gene has an effect from the early time of the formation of siliques that actually forms seeds (FIG. 4b).

Example 4

Preparation of *Arabidopsis thaliana* Transformants that Overexpress AtABCA9/AtATH11 Gene In reference of Example 1, serving the gDNA as a template that was extracted from the wild-type *Arabidopsis thaliana* (Columbia-0, SALK institute), AtABCA9/AtATH11 gene was amplified by PCR (25 cycles of 95° C. 30 sec, 56° C. 30 sec, 72° C. 2.5 min) using AtATH11-ATG (SEQ ID NO: 8: 5'-ACTAGTATGACTCTGCGAGAAGGCTT-3') and AtATH11-Stop (SEQ ID NO: 9: 5'-ACTAGTTTAATTGT-TAGATTCATAATCA-3') primers, and T-blunt vector (Solgent, http://www.solgent.co.kr/) was added, and was recombined in pCAMBIA1302 binary vector (Cambia, http://www.cambia.org/daisy/cambia/585.html using SpeI (Roche, http://www.roche.co.kr/portal/kr). pCAMBIA1302 vector was used as plant expression vector to produce *Arabidopsis thaliana* transformants and this contains a CaMV 35S promoter, a multi-cloning site, and a nopaline synthetase terminator.

Using the floral dipping method (Clough and Bent, 1988), *Agrobacterium* (GV3101) (obtained from Cauliflower mosaic virus (CaMV)) that contains pCAMBIA1302: AtABCA9/AtATH11 gene was used to transform into *Arabidopsis thaliana*. The transformed seed was selected in ½ MS (Murashige and Skoog, 1962) medium containing 50 μg/L kanamycin antibiotics, and the seeds were taken from the plants survived. Homozygote seeds in the $3^{rd}$ generation were used for phenotype analysis.

Example 5

Quantitative RT-PCR

Example 5-1

RNA Isolation and cDNA Synthesis

<Preparation of *Arabidopsis thaliana* Sample>

1) Samples to Measure the Expression of AtABCA9/AtATH11 by Tissues

To measure the expression of AtABCA9/AtATH11 protein according to tissues, samplings of each tissues (WS: whole seedling grown for 2 weeks in a medium, L: leaves grown for 2 weeks in a medium and for 2 weeks in soil, S: stems grown for 2 weeks a medium and for 3 weeks in soil, F: flowers grown for 2 weeks in a medium and for 3 weeks in soil, S1: siliques 4~6 DAF, S2: siliques 10~12 DAF, and S3: siliques 16~18 DAF, DAF: Day After Flowering) of wild-type *Arabidopsis thaliana*(Columbia-0, SALK institute) were done, and were used for RNA isolation and cDNA synthesis.

2) Samples for Measuring Expression of Overexpressing-Transformants

To measure the expression of overexpressing-transformants, the wild-type *Arabidopsis thaliana* and the *Arabidopsis thaliana* transformants which was produced according to the Example 4 were cultured for 6 weeks, and samplings were done on each siliques, and were used for total RNA isolation and cDNA synthesis.

<RNA Isolation and cDNA Synthesis>

After 100 mg of *Arabidopsis thaliana* samples of 1) and 2) were evenly pulverized using liquid nitrogen, the pulverized samples were placed in 2 ml tubes, and were well mixed with 800 μl of an RNA extraction buffer (p-aminosalicylic acid 2.7 g, triisopropyl naphthalene sulfonic acid 0.45 g, 1.25 M Tris HCl pH 9.0, 1.25 M NaCl, 0.25 M EDTA, β-mercaptoethanol 1 ml, acidic phenol 1.2 ml, DEPC water 36 ml) and 400 μl of acidic phenol. After inserting 400 μl of chloroform and well blended, place it in ice for 10 min. After centrifugation at 6000 rpm in 4° C. for 10 min, the supernatant was transferred to a fresh tube, and 200 μl of isopropanol was added. After centrifugation at 6000 rpm in 4° C. for 15 min, the supernatant was removed and the pellet was dried.

After the dried pellet was treated with DNase (Roche, http://www.roche.co.kr/portal/kr), 50 μl of RNase-free water was inserted to the tube, and the pellet was dissolved to earn RNA.

To the 2 μg of RNA obtained from above, cDNA was synthesized using Powerscript RT (reverse transcription)-kit (BD Bioscience Clontech) and oligo dT primer according to the manufacturer's instruction.

Example 5-2

Quantitative RT-PCR

To know the expression pattern by tissues of AtABCA9/AtATH11 gene and the level of expression of the overexpressing transformants, each cDNA of wild-type and transformants through Example 5-1 were served as template, and quantitative RT-PCR was performed (45 cycles of 94° C. 30 sec, 56° C. 15 sec, 15° C. sec) using the AtABCA9/AtATH11 F1 primer (SEQ ID NO: 10: 5'-ATGACTCTGCGAGAAG-GCTT-3') and AtABCA9/AtATH11 R1 primer (SEQ ID NO: 11: 5'-CATGGAAGAATCGGAAGAGA-3').

As a results of measuring the expression patterns according to tissues of AtABCA9/AtATH11 protein (WS, whole seedling; L, leave; S, stem; F, flower; S1, siliques 4~6 DAF; S2, siliques 10~12 DAF; and S3, siliques 16~18 DAF, DAF; Day After Flowering) AtABCA9/AtATH11 gene showed a higher expression level in silique compared to other tissues (FIG. 5a), and according to the level of expression of overexpressing transformants, expression of AtABCA9/AtATH11 gene at overexpressing transformants (T1~T12 in FIG. 5b) is significantly higher compared to the wild-type (WT in FIG. 5b). ubiquitin 1 (AY059080) was used as a control plot.

Example 6

Measurement of Fat store in Seeds

To measure the fat store in the seeds of mutants that can't express AtABCA9/AtATH11 protein identified in Example 1 and wild-type (Columbia-0, SALK institute), stored oils were extracted from 300 seeds of each. 300 seeds were put in 1 mL of 2-propanol and were boiled at 80° C. for 5 min, and were chilled, and then 2 mL of chloroform was added and were grinded finely with Polytron Homogenizer. And then, after it was centrifuged at 3,000 rpm in room temperature for 10 min, the supernatant was collected, and 0.9% (v/v) of KCl was added and shaken, followed by centrifugation at 3,000 rpm in room temperature for 10 min.

When the solvent was evaporated after the lower layer was collected, only the oil remained, and by weighing this the total weight of oil could be measured (FIG. 6a), and then was dissolved by chloroform, and 1 mg of the oil was loaded to a TLC plate (Merck 1.05721). In order to observe the triacylglycerol, a main neutral fat of a seed, 90 ml of hexane, 7.5 ml of diethylether, and 1 ml of acetic acid were mixed in a glass tank as a solvent to separate neutral fat, and then deployed inserting TLC plate that loaded samples. After deployment, the TLC plate was stained with primuline and triacylglycerol was observed under UV light. Triacylglycerol was scraped off from the TLC plate and after it was dissolved in 3 mL of hexane, the quantity of triacylglycerol which is a main oil constituent was measured using gas chromatography (FIG. 6b).

As can be seen in FIGS. 6a and 6b, for mutants that can't express AtABCA9/AtATH11 protein, the total weight of seed and total fat (or oil) decreased but didn't show much difference in protein content compared to wild-type (FIG. 6a), and for triacylglycerol, which is a main fat store (or oil) of seeds, decreased about 35% in mutants compared to wild-type (FIG. 6b). These results indicate that AtABCA9/AtATH11 protein plays an important role in the fat store of seed.

Example 7

Productivity Measurement of Overexpressing Transformants

To compare the productivity of the transformants that overexpresses the AtABCA9/AtATH11 gene produced in Example 4, the seeds from wild-type *Arabidopsis thaliana* (Columbia-0, SALK institute) and the transformed *Arabidopsis thaliana* were stored for 2 days after the surfaces were sterilized with ethanol and chlororox, at 4° C. in a dark place, and then was cultured in ½ MS medium (Murashige and Skoog 1962). After the medium was cultured horizontally for 2 weeks (16 h light/8 h dark, 22° C./18° C.), they were transferred to soil and were grown for 4 weeks and the growth rate, the number of siliques, the number of seeds per silique, the size and weight of seeds, and the TAG content in seeds were measured and compared from wild-type and transformants. The TAG measurement was done by extracting TAG using seeds from wild-type and overexpressing transformants according to the method disclosed in Example 6.

Figure 7:
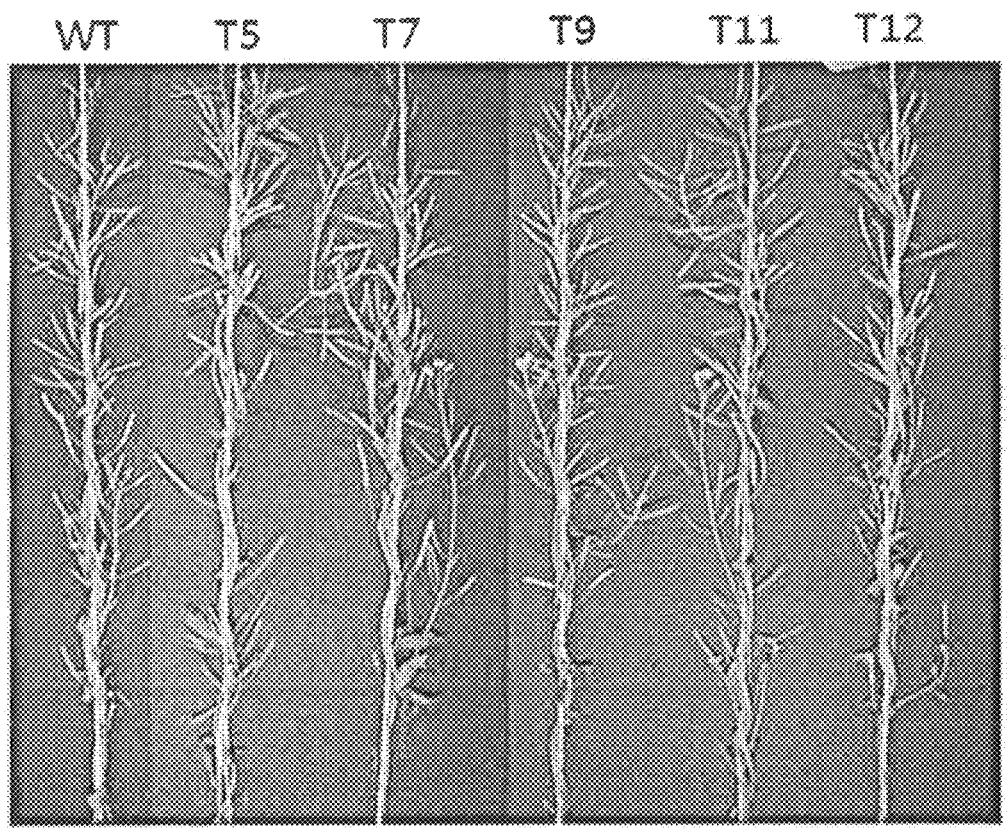
FIG. 7 shows the result of observing the plant growth of wild species and transformants that overexpress AtABCA9/AtATH11 protein in accordance with Example 7 (WT: wild-type, T5, T7, T9, T11 and T12 overexpression transformants).
Figure 8:
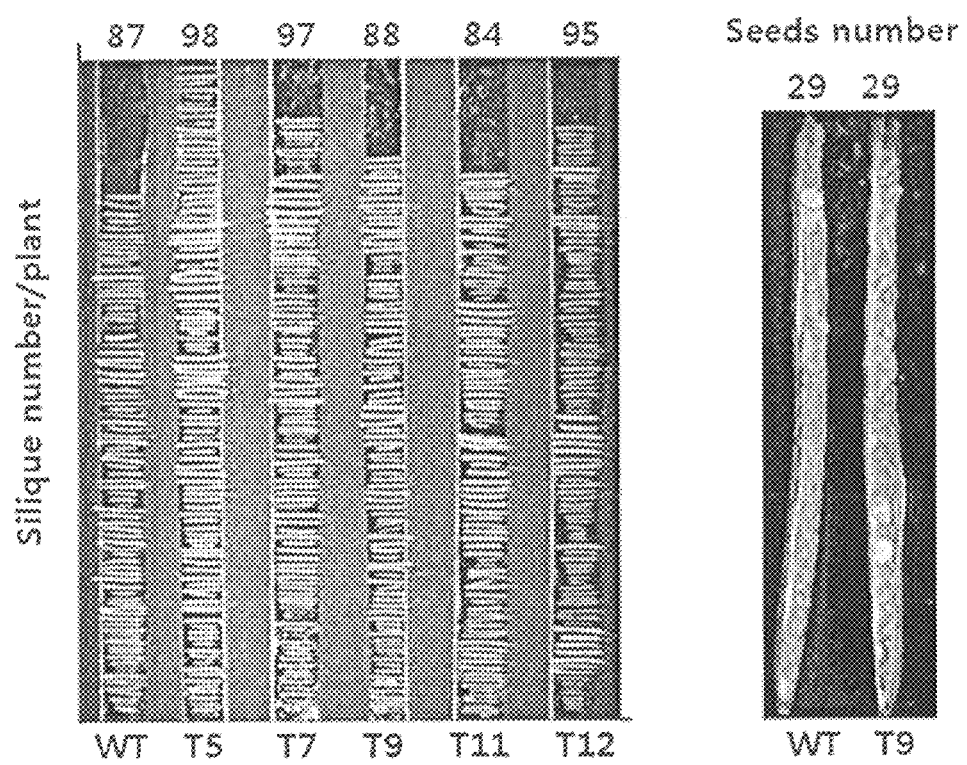
FIG. 8 shows the result of observing the number of siliques and the number of seeds in the silique of wild species and transformants that overexpress AtABCA9/AtATH11 protein in accordance with Example 7 (WT: wild-type, T5, T7, T9, T11 and T12: overexpression transformants).

As a result, the growth of plants were similar between wild type (WT) and overexpressing transformants (T5, T7, T9, T11 and T12) or transformants showed slightly higher growth (FIG. 7, and when the number of siliques and the number of seeds in the silique were compared, the number of siliques was increased by 6.2% on average in the overexpressing transformants, while there were no difference in the number of seeds per silique therebetween (FIG. 8).

In addition, for the overexpressing transformants (T5 and T8), the seeds in silique became much bigger in size (FIG. 9a) compared to wild type, and especially the transformants T8 showed increase up to 123% (FIG. 9b) in seed weight, compared to the wild-type. Also, the transformants, particularly T9, contained triactylglycerols (TAG), which is the main fat store of seed, in an amount 132% higher than that of the wild-type (FIG. 9c).

Consequently, the transformants that overexpress AtABCA9/AtATH11 gene of the present invention showed significant increase in the number of silique, the size of seeds in siliques, and the content of TAG, although there hasn't been much difference in the number of seeds per silique, and thus identified a great improvement in view of total productivity and fat store.

INDUSTRIAL APPLICABILITY

The present invention can significantly improve the productivity of vegetable fat (or oil) in a limited space since it could more increase the fat store content in seeds through the increase of content itself of the fat store (or oil) stored in plant seed and the increase of seed in size which is a main storage organ of vegetable oil. And thus can make a significant contribution to the supply of biodiesel and edible plant fats (or oils) in response to the rapidly increasing demand therefor.

The invention claimed is:

1. A method for increasing plant seeds in size and storing fat content, comprising introducing a polynucleotide encoding a plant ATP-binding cassette (ABC) transporter protein comprising the amino acid sequence of SEQ ID NO: 1 that is operably linked to a promoter for overexpressing the protein in a plant.

2. The method of claim 1, wherein the polynucleotide is SEQ ID NO: 2.

3. The method of claim 1, wherein the storage fat is a triacylglycerol.

4. The method of claim 1, wherein the plant is rice, wheat, barley, corn, soybean, red bean, oat, sorghum, onion, carrot, cucumber, olive, sweet potato, potato, Chinese cabbage, radish, lettuce, broccoli, tobacco, petunia, sunflower, leaf mustard, turf, *Arabidopsis thaliana, Brassica campestris, B. napus, Betula platyphylla*, poplar, hybrid poplar, or *Betula schmidtii*.

* * * * *